United States Patent
Fryer et al.

[11] B 3,989,681
[45] Nov. 2, 1976

[54] 7-AZOXY SUBSTITUTED-1,4-BENZODIAZEPIN-2-ONES

[75] Inventors: Rodney Ian Fryer, North Caldwell; Armin Walser, West Caldwell, both of N.J.

[73] Assignee: Hoffmann-La Roche Inc., Nutley, N.J.

[22] Filed: Nov. 28, 1973

[21] Appl. No.: 419,582

[44] Published under the second Trial Voluntary Protest Program on March 2, 1976 as document No. B 419,582.

[52] U.S. Cl............ 260/143; 260/239.3 D; 424/226
[51] Int. Cl.$^2$............ C07C 107/04
[58] Field of Search............ 260/143, 152; 424/226

[56] References Cited
UNITED STATES PATENTS

| | | | |
|---|---|---|---|
| 3,567,710 | 3/1971 | Fryer et al. | 260/239.3 |
| 3,784,542 | 1/1974 | Hellerbach et al. | 260/239.3 D |

OTHER PUBLICATIONS
Roth et al., Chemical Abstracts, vol. 71, (1969), 112898w.

*Primary Examiner*—Charles F. Warren
*Attorney, Agent, or Firm*—Samuel L. Welt; Frank P. Hoffman

[57] ABSTRACT

Novel 1,4-benzodiazepin-2-ones of the formula

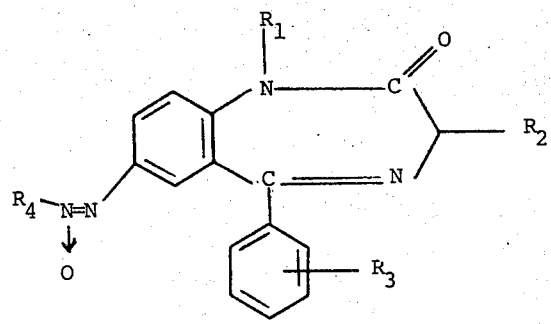

wherein
$R_1$ is selected from the group consisting of hydrogen, lower alkyl, cycloalkyl-lower alkyl, hydroxylower alkyl, lower alkoxy-lower alkyl and di-lower alkylamino-lower alkyl;
$R_2$ signifies hydrogen or lower alkyl; $R_3$ signifies hydrogen or halogen; $R_4$ signifies lower alkyl
and the pharmaceutically acceptable acid addition salts thereof, are disclosed together with processes for preparing these compounds and novel intermediates used in these processes. These 7-azoxy substituted-1,4-benzodiazepin-2-ones are useful as muscle relaxant, anti-convulsant and sedative agents.

3 Claims, No Drawings

7-AZOXY SUBSTITUTED-1,4-BENZODIAZEPIN-2-ONES

DETAILED DESCRIPTION OF THE INVENTION

The present invention relates to novel 1,4-benzodiazepine derivatives bearing an azoxy substituent in the 7-position. This invention further comprehends processes for making these novel benzodiazepines and novel intermediates employed in these processes.

More specifically, the compounds of the present invention are selected from the group consisting of compounds of the formula

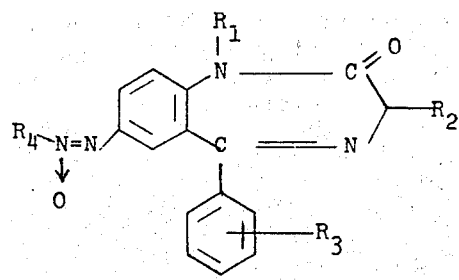

I wherein
R$_1$ is selected from the group consisting of hydrogen, lower alkyl, cycloalkyl-lower alkyl, hydroxy-lower alkyl, lower alkoxy-lower alkyl and di-lower alkylamino-lower alkyl;
R$_2$ signifies hydrogen or lower alkyl; R$_3$ signifies hydrogen or halogen; R$_4$ signifies lower alkyl and the pharmaceutically acceptable acid addition salts thereof.

As used herein, the term "lower alkyl" either alone or in combination refers to straight and branched chain hydrocarbon groups containing from 1 to 7 preferably from 1 to 4 carbon atoms such as, for example, methyl, ethyl, propyl, isopropyl, isobutyl, butyl and the like. The term "halogen" refers to all four forms thereof, ie. bromine, chlorine, fluorine and iodine. The term "lower alkoxy" designates straight or branched chain saturated hydrocarbonoxy groups containing from 1 to 7 carbon atoms, preferably 1 to 4 carbon atoms such as methoxy, ethoxy, propoxy and the like. The term "cycloalkyl" refers to cycloalkyl groups containing from 3 to 7 carbon atoms such as cyclopropyl, cyclobutyl, cyclopentyl and the like.

Preferred among the compounds falling within the scope of formula I above are those wherein R$_2$ signifies hydrogen and R$_3$ is located at the ortho position of the 5-phenyl ring, i.e. compounds of the formula

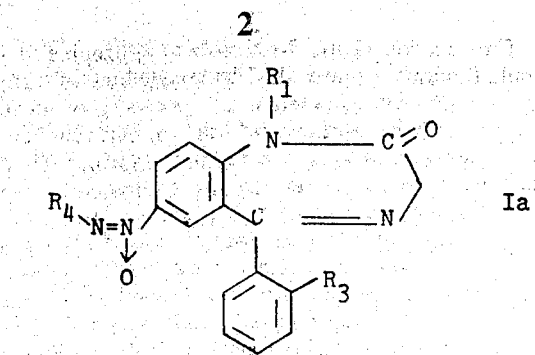

Ia wherein R$_1$, R$_3$ and R$_4$ are as described above.

When the R$_1$ substituent signifies lower alkyl, methyl is preferred; when R$_1$ signifies hydroxy lower alkyl, hydroxyethyl is preferred; when R$_1$ signifies lower alkoxy -lower alkyl, methoxymethyl is preferred; when R$_1$ signifies cycloalkyl-lower alkyl, cyclopropylmethyl is preferred and when R$_1$ signifies di-lower alkylamino lower alkyl, diethylaminoethyl is preferred. When the R$_3$ substituent is halogen, chlorine and fluorine are preferred. The preferred lower alkyl group for the R$_4$ substituent is methyl.

Representative of compounds of formula I above are: 1,3-dihydro-7-(N-methyl-N-oxyazo)-1-methoxymethyl-5-phenyl-2H-1,4-benzodiazepin -2-one; 1,3-dihydro-7-(N-methyl-N-oxyazo)-1-methyl-5-phenyl-2H-1,4-benzodiazepin-2-one; 1,3-dihydro-7-(N-methyl-N-oxyazo)-1-methoxymethyl-5-(orthofluorophenyl)-2H-1,4-benzodiazepin-2-one; 1,3-dihydro-7-(N-methyl-N-oxyazo)-1-methoxymethyl-5-(orthochlorophenyl)-2H-1,4-benzodiazepin-2-one; and 1,3-dihydro-7-(N-ethyl-N-oxyazo)-1-methoxymethyl-5-phenyl-2H-1,4-benzodiazepin-2-one.

The compounds of formula I above may be prepared by reacting the corresponding 7-nitrosobenzodiazepine of the formula

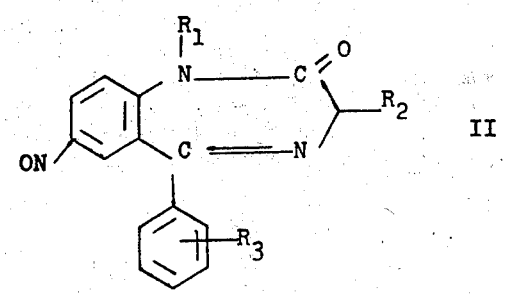

II wherein R$_1$ through R$_3$ are as described above
with a lower alkyl hydroxylamine of the formula

R$_4$ — NHOH    III wherein R$_4$ is as described above.

The reaction of the 7-nitrosobenzodiazepine of formula II with the lower alkyl hydroxylamine of formula III is preferably effected in the presence of an inert organic solvent. Suitable solvents for this reaction include hydrocarbons such as hexane, chlorinated hydrocarbons such as chloroform and methylene chloride, alcohols such as methanol, ethanol, propanol and the like, ethers such as tetrahydrofuran and dimethylformamide. Temperature is not critical to this process aspect, and thus temperatures from room temperature to the reflux temperature of the reaction medium can be employed with the reflux temperature being preferred. Representative of the compounds of formula III suitable for the purposes of the present invention are methylhydroxylamine, ethylhydroxylamine, propylhydroxylamine etc.

The starting materials of formula II above may be prepared by the oxidation of the corresponding 7-hydroxyamino-1,4-benzodiazepin-2-one of the formula

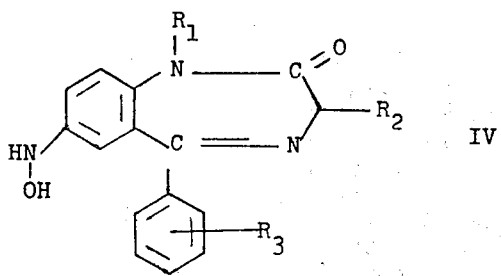

IV wherein $R_1$ through $R_3$ are as described above.

The conversion of the 7-hydroxyaminobenzodiazepine of formula IV to the corresponding 7-nitroso compound is effected by treating the compound of formula IV with an oxidizing agent. Suitable oxidizing agents for the purposes of this process aspect include ferric chloride, manganese dioxide, cupric chloride and the like with manganese dioxide being preferred. This oxidation is preferably effected in the presence of an inert organic solvent. Suitable solvents include hydrocarbons such as hexane, ethers such as tetrahydrofuran and chlorinated hydrocarbons such as chloroform and methylene chloride. Temperature is not critical to this process aspect, and thus the reaction is expediently effective at room temperature.

The 7-nitrosobenzodiazepin-2-ones of formula II are novel and as such form a part of the present invention.

The 7-hydroxyaminobenzodiazepines of formula IV used as intermediates in the preparation of the desired starting materials of formula II are prepared by the selective reduction of the corresponding 7-nitrobenzodiazepin-2-one of the formula

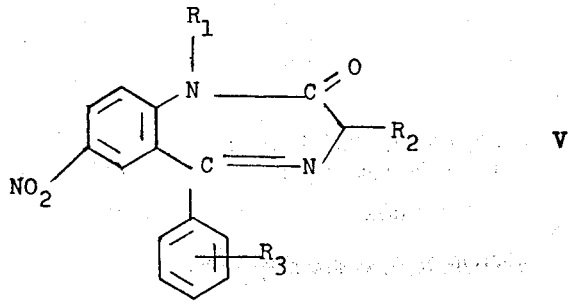

V wherein $R_1$ through $R_3$ are as described above.

The 7-nitrobenzodiazepine derivatives of formula V above are known compounds or can be prepared in analogy to the preparation of the known materials. The reduction of the 7-nitro group to the desired hydroxyamino group is accomplished by selective chemical or catalytic reducing systems. Suitable reducing systems for the present purposes include zinc in ammonium chloride and stannic chloride in a buffered system. Acetate, citrate or phosphate buffers are suitable with sodium acetate being preferred. This reduction is preferably effected in the presence of an inert organic solvent. Representative of the solvents that can be employed are alcohols, such as methanol, ethanol and the like, water, ether such as tetrahydrofuran, hydrocarbons such as hexane and the like, chlorinated hydrocarbons such as chloroform, methylene chloride and the like, acetone, dimethylformamide and dimethylsulfoxide. Temperature is not critical to this process aspect, so that temperatures above or below room temperature can be employed with room temperature being preferred.

The compounds of formula I above form pharmaceutically acceptable acid addition salts with organic and inorganic acids, thus the compounds of the present invention form pharmaceutically acceptable acid addition salts with inorganic acids such as hydrohalic acids, for example, hydrochloric acid and hydrobromic acid and with organic acids such as tartaric acid, citric acid, camphorsulfonic acid, ethanesulfonic acid, toluenesulfonic acid salicyclic acid, ascorbic acid, maleic acid, succinic acid, formic acid, acetic acid and the like.

The compounds of formula I above as well as their pharmaceutically acceptable acid addition salts are useful as anti-convulsant, muscle relaxant and sedative agents. Thus, the compounds of the present invention and their pharmaceutically acceptable salts can be used as medicaments. For example, they can be used in the form of pharmaceutical preparations which contain them or their salts in ad-mixture with a pharmaceutical organic or inorganic carrier material which is suitable for enteral or parenteral application such as, for example, water, gelatin, lactose, starches, magnesium sterate, talc, vegetable oils, gum arabic, polyalkyleneglycols, vaseline, etc. The pharmaceutical preparations can be prepared in solid form (e.g. as tablets, dragees, suppositories, capsules) or in liquid form (e.g. as solutions, suspensions or emulsions). They may be sterilized and/or contain additives such as preserving, stabilizing, wetting or emulsifying agents, salts for varying the osmotic pressure or buffers. They can also contain other therapeutically valuable substances.

The compounds of formula I above or their pharmaceutically acceptable salts can be administered at dosages adjusted to individual requirements and fitted to the pharmaceutical exigencies of the situation. Convenient pharmaceutical dosages are in the range of from about 2 mg. to about 200 mg. per day.

The useful anticonvulsant activity of the compounds of formula I above is shown in warm blooded animals utilizing the standard antimetrazole test. This test was carried out according to the method of Everett and Richard (J.P.E.T., 81: 402, 1944). The $ED_{50}$ was calculated as the dose which would prevent convulsions in 50% of the mice tested after administration of 125 mg/kg of pentylenetetrazole by the subcutaneous route. Following these test procedures 1,3-dihydro-7-(N-methyl-N-oxyazo)-1-methoxymethyl-5-phenyl-2H-1,4-benzodiazepin-2-one (Compound A) shows an $ED_{50}$ of 60 ± 14 indicating that this compound exhibits anticonvulsant activity.

The sedative and muscle relaxant activity of the compounds of formula I above are shown using the standard foot shock test. In this test a pair of mice is confined under a 1 liter beaker placed on a grid which presents shock to the feet. At least five fighting episodes are elicited in a two minute period. Pairs of mice are marked and pretreated 1 hour prior to a second shock. Logarithmic dose intervals are utilized up to a maximum of 100 mg/kg. At the 100% blocking dose, three out of three pairs must be blocked from fighting. The measurements are made at the dose level at which 100% blocking is observed and the results are expressed as the dose in mg/kg ($PD_{50}$) which blocks the fighting response for 1-hour. Following these test procedures, compound A exhibits a $PD_{50}$ of 50 mg/kg, indicating that this compound exhibits sedative and muscle-relaxant activity.

The following examples are illustrative of the present invention. All temperatures are given in degrees Centigrade.

EXAMPLE 1

Preparation of
1,3-dihydro-7-hydroxyamino-1-methoxymethyl-5-phenyl-2H-1,4-benzodiazepin-2-one A mixture of 33 g. (0.1 mol) of 1,3-dihydro-1-methoxymethyl-7-nitro-5-phenyl-2H-1,4-benzodiazepin-2-one, 1 l. of tetrahydrofuran, 1 l. of methanol. 113 g. (0.5 mol) of stannous chloride dihydrate and 136 g. (1 mol) of sodium acetate trihydrate was stirred at room temperature for 6 hrs. under an atmosphere of nitrogen. The inorganic salts were separated by filtration over celite. The filtrate was evaporated and the residue was partitioned between methylene chloride and 1N sodium hydroxide solution. The methylene chloride layer was washed with water, dried and evaporated. Crystallization of the residue from methylene chloride/ether yielded light yellow product with m.p. 168°–170°. For analysis it was recrystallized from the same solvents, m.p. 168°–171°.

EXAMPLE 2

Preparation of
1,3-dihydro-7-hydroxyamino-5-phenyl-2H-1,4-benzodiazepin-2-one

A mixture of 16.8 g. of 1,3-dihydro-7-nitro-5-phenyl-2H-1,4-benzodiazepin-2-one, 500 ml. of tetrahydrofuran, 250 ml. of methanol, 56 g. of stannous chloride dihydrate and 68 g. of sodium acetate trihydrate was stirred at room temperature under an atmosphere of nitrogen for 24 hours. 1 l. of tetrahydrofuran and 15 ml. of concentrated ammonia were then added. The inorganic salts were removed by filtration through celite. The filtrate was evaporated. The solid residue was stirred with 100 ml. of methylene chloride and 250 ml. of water for 20 minutes under nitrogen. The insoluble crystals were collected to leave light yellow material. For analysis it was recrystallized from ethanol/methylene chloride, m.p. 186°–187°.

EXAMPLE 3

Preparation of
1,3-dihydro-7-hydroxyamino-1-methyl-5-phenyl-2H-1,4-benzodiazepin-2-one A mixture of 15 g. (0.05 mol) of 1,3-dihydro-1-methyl-7-nitro-5-phenyl-2H-1,4-benzodiazepin-2-one, 250 ml. of tetrahydrofuran, 250 ml. of methanol, 56 g. of stannous chloride dihydrate and 68 g. of sodium acetate trihydrate was stirred under nitrogen for 3 hours. 1 l. of methylene chloride and 15 ml. of concentrated ammonia was added. The inorganic material was separated by filtration over celite. The filtrate was washed with 1N sodium hydroxide solution, was dried over sodium sulfate and evaporated. Crystallization of the residue from methylene chloride and recrystallization from ethanol/methylene chloride yielded light yellow product with m.p. 211°–213°.

EXAMPLE 4

Preparation of
1,3-dihydro-5-(2-fluorophenyl)-7-hydroxyamino-1-methyl-2H-1,4-benzodiazepin-2-one A mixture of 16 g. (0.05 mol) of 1,3-dihydro-5-(2-fluorophenyl)-1-methyl-7-nitro-2H-1,4-benzodiazepin-2-one, 500 ml. of tetrahydrofuran, 250 ml. of methanol, 68 g. of sodium acetate trihydrate and 56 g. of stannous chloride dihydrate was stirred under nitrogen for 6 hours. 25 ml. of concentrated ammonia was added and the inorganic salts were removed by filtration through celite. The filtrate was washed well with 2 l. of tetrahydrofuran. The filtrate was evaporated and the solid residue was dissolved in ethanol/tetrahydrofuran. The solution was again filtered with celite and concentrated. The separated crystals were collected to leave light yellow product. For analysis it was recrystallized from ethanol/tetrahydrofuran, m.p. 228°–230° dec.

EXAMPLE 5

Preparation of
5-(2-chlorophenyl)-1,3-dihydro-7-hydroxyamino-1-methoxymethyl-2H-1,4-benzodiazepin-2-one A mixture of 3.6 g. (0.01 mol) of 5-(2-chlorophenyl)-1,3-dihydro-1-methoxymethyl-7-nitro-2H-1,4-benzodiazepin-2-one, 100 ml. of tetrahydrofuran, 50 ml. of methanol, 13.6 g. of sodium acetate trihydrate and 11.25 g. of stannous chloride dihydrate was stirred under nitrogen for 5 hours. 500 ml. of methylene chloride and 10 ml. of concentrated ammonia was added. The inorganic material was separated by filtration. The filtrate was washed with 1N sodium hydroxide solution, dried over sodium sulfate and evaporated. Crystallization of the residue from methylene chloride/ether gave light yellow product with m.p. 205°–208° dec. For analysis it was recrystallized from 2-propanol/tetrahydrofuran.

EXAMPLE 6

Preparation of
1,3-dihydro-1-methoxymethyl-7-nitroso-5-phenyl-2H-1,4-benzodiazepin-2-one 30 g. of Manganese dioxide was added to a solution of 3.1 g. (0.01 mole) of 1,3-dihydro-7-hydroxyamino-1-methoxymethyl-5-phenyl-2H-1,4-benzodiazepin-2-one in 200 ml. of methylene chloride. After stirring for 10 minutes at room temperature the inorganic material was filtered off and the filtrate was evaporated to leave an oil with a greenish tint. Since crystallization attempts were unsuccessful the material was purified by chromatography over 50 g. of silica gel using 5% ethylacetate in methylene chloride. The thin layer chromatographically pure fractions still did not crystallize.

EXAMPLE 7

Preparation of
1,3-dihydro-7-(N-methyl-N-oxyazo)-1-methoxymethyl-5-phenyl-2H-1,4-benzodiazepin-2-one A mixture of 9.3 g. (0.03 mol) of 1,3-dihydro-7-hydroxyamino-1-methoxymethyl-5-phenyl-2H-1,4-benzodiazepin-2-one, 300 ml. of methylene chloride and 100 g. of manganese dioxide was stirred for 10 minutes at room temperature. The reaction mixture was filtered through celite into a mixture of 7.5 g. (0.09 mol) methylhydroxyamine hydrochloride, 15 g. of sodium acetate and 100 ml. of ethanol. The methylene chloride was partially evaporated under reduced pressure and the remaining solution was heated on the steam bath for 10 minutes. The residue obtained after complete evaporation was partitioned between methylene chloride and aqueous sodium bicarbonate solution. The organic layer was dried and evaporated. The residue was chromatographed over 250 g. of silica gel with 10% ethylacetate in methylene chloride. Crystallization of the pure fractions from ether/hexane yielded colorless product with m.p. 110°–115°.

EXAMPLE 8

Capsule Formulation

| | Per Capsule |
|---|---|
| 1,3-Dihydro-7-(N-methyl-N-oxyazo)-1-methoxymethyl-5-phenyl-2H-1,4-benzodiazepin-2-one | 50 mg |
| Lactose, USP | 125 mg |
| Corn Starch, USP | 30 mg |
| Talc, USP | 5 mg |
| Total Weight | 210 mg |

Procedure:

1. The drug was mixed with lactose and corn starch in a suitable mixer.
2. The mixture was further blended by passing through a Fitzpatrick Comminuting machine with a No. 1A screen with knives forward.
3. The blended powder was returned to the mixer, the talc added and blended thoroughly.
4. The mixture was filled into No. 4 hard shell gelatin capsules on a Parke Davis capsulating machine.

EXAMPLE 9

Capsule Formulation

| | Per Capsule |
|---|---|
| 1,3-Dihydro-7-(N-methyl-N-oxyazo)-1-methoxymethyl-5-phenyl-2H-1,4-benzodiazepin-2-one | 10 mg |
| Lactose | 158 mg |
| Corn Starch | 37 mg |
| Talc | 5 mg |
| Total Weight | 210 mg |

Procedure:

1. The drug was mixed with the lactose and corn starch in a suitable mixer.
2. The mixer was further blended by passing through a Fitzpatrick Comminuting machine with a No. 1A screen with knives forward.
3. The blended powder was returned to the mixer, the talc added and blended thoroughly. The mixture was then filled into No. 4 hard shell gelatin capsules on a Parke Davis capsulating machine. (Any similar type machine may be used).

EXAMPLE 10

Tablet Formulation

| | Per Tablet |
|---|---|
| 1,3-Dihydro-7-(N-methyl-N-oxyazo)-1-Methoxymethyl-5-phenyl-2H-1,4-benzodiazepin-2-one | 25.00 mg |
| Lactose, USP | 64.50 mg |
| Corn Starch | 10.00 mg |
| Magnesium Stearate | 0.50 mg |
| Total Weight | 100.00 mg |

Procedure:

1. The drug was mixed with the lactose, corn starch and magnesium stearate in a suitable mixer.
2. The mixture was further blended by passing through a Fitzpatrick Comminuting machine fitted with a No. 1A screen with knives forward.
3. The mixed powders were slugged on a tablet compressing machine.
4. The slugs were comminuted to a mesh size (No. 16 screen) and mixed well.
5. The tablets were compressed at a tablet weight of 100 mg using tablet punches having a diameter of approximately one-fourth inch. (Tablets may be either flat or biconvex and may be scored if desired).

EXAMPLE 11

Tablet Formulation

| | Per Tablet |
|---|---|
| 1,3-Dihydro-7-(N-methyl-N-oxyazo)-methoxymethyl-5-phenyl-2H-1,4-benzodiazepin-2-one | 10.0 mg |
| Lactose | 113.5 mg |
| Corn Starch | 70.5 mg |
| Pregelatinized Corn Starch | 8.0 mg |
| Calcium Stearate | 3.0 mg |
| Total Weight | 205.0 mg |

Procedure:

1. The drug was mixed with the lactose, corn starch and pregelatinized corn starch in a suitable size mixer.
2. The mix was passed through a Fitzpatrick Comminuting machine fitted with No. 1A screen and with knives forward.
3. The mix was returned to the mixer and moistened with water to a thick paste. The moist mass was passed through a No. 12 screen and the moist granules were dried on paper lined trays at 110°F.
4. The dried granules were returned to the mixer, the calcium stearate was added, and mixed well.

5. The granules were compressed at a tablet weight of 200 mg using standard concave punches having a diameter of five-sixteenths inch.

We claim:
1. A compound of the formula

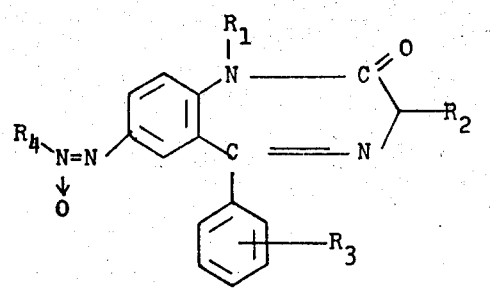

wherein
- $R_1$ is selected from the group consisting of hydrogen, lower alkyl, $C_3$ to $C_7$ cycloalkyl-lower alkyl, hydroxy-lower alkyl, lower alkoxy-lower alkyl and dilower alkylamino-lower alkyl;
- $R_2$ signifies hydrogen or lower alkyl;
- $R_3$ signifies hydrogen or halogen;
- $R_4$ signifies lower alkyl or the pharmaceutically acceptable acid addition salts thereof.

2. The compound of claim 1 which is 1,3-dihydro-7-(N-methyl-N-oxyazo)-1-methoxymethyl-5-phenyl-2H-1,4-benzodiazepin-2-one.

3. The compound of claim 1 which is 1,3-dihydro-7-(N-lower alkyl-N-oxyazo)-1-lower alkoxy-lower alkyl-5-(orthohalophenyl)-2H-1,4-benzodiazepin-2-one.

* * * * *